United States Patent [19]

Carter et al.

[11] 4,427,380
[45] Jan. 24, 1984

[54] METHOD AND APPARATUS FOR THE GENERATION OF DIFFERENTIAL DISTAL MOVEMENT OF TEETH

[76] Inventors: Philip W. Carter, Box 357, St. Anne, Manitoba, Canada, R0A 1R0; Kenneth McLachlan, Box 150, St. Adolphe, Manitoba, Canada, R0A 1S0

[21] Appl. No.: 416,845

[22] Filed: Sep. 13, 1982

[51] Int. Cl.³ .................................................. A61C 7/00
[52] U.S. Cl. ........................................................ 433/5
[58] Field of Search ............................................ 433/5

[56] References Cited

U.S. PATENT DOCUMENTS 4,040,188  9/1977  Forster .................................... 433/5
4,167,061  9/1979  Masel ..................................... 433/5

Primary Examiner—Robert Peshock
Attorney, Agent, or Firm—Stanley G. Ade

[57] ABSTRACT

A buttressed or augmented neck strap is used and comprises a wedge-shaped portion on one side of the neck strap. The strap includes a resilient strap connected by the outer ends thereof to the ends of an outer facial bow which has an inner dental bow connected thereto so that the force on the side that includes the wedge is applied to the same side of the facial bow and hence to the inner bow, offset from the tangent of the neck of the patient thus giving the desired differential force without undesirable side effects being produced.

40 Claims, 5 Drawing Figures

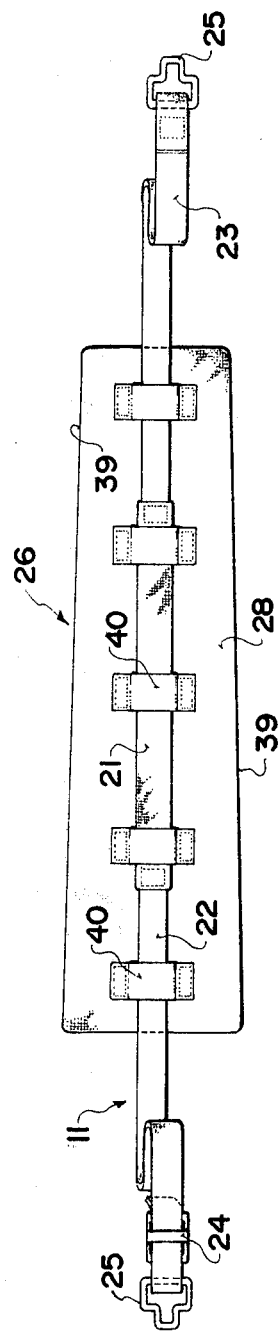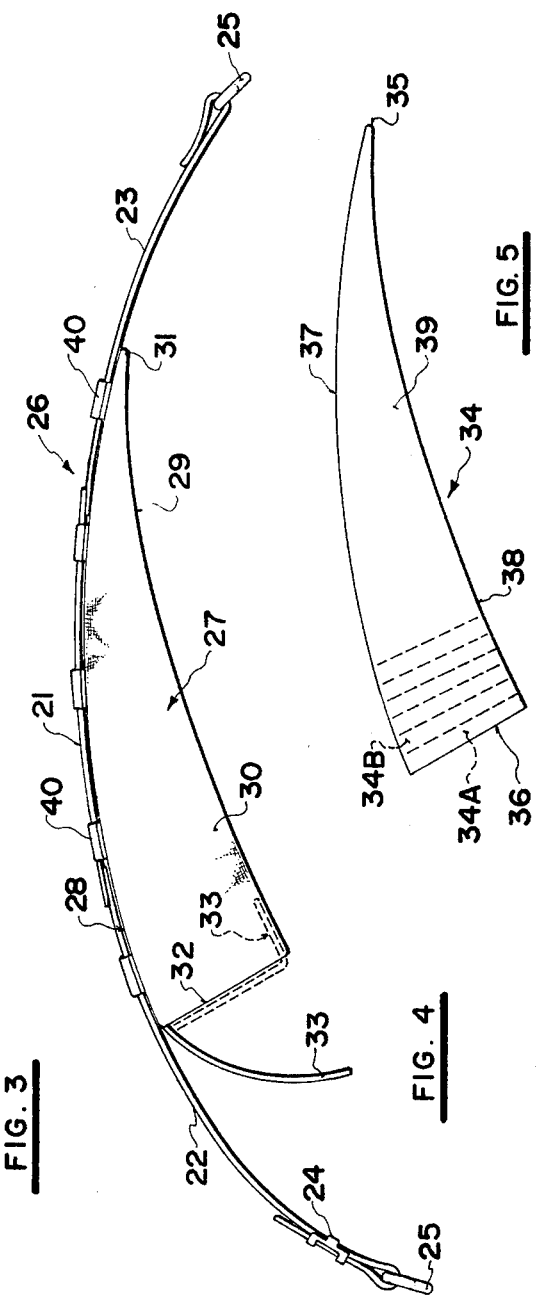

METHOD AND APPARATUS FOR THE GENERATION OF DIFFERENTIAL DISTAL MOVEMENT OF TEETH

BACKGROUND OF THE INVENTION

This invention relates to new and useful improvements in orthodontics, and in particular, the portion of orthodontics relating to the generation of differential distal movement of teeth.

Conventionally, extra-oral anchorage is used for the movement of teeth in which opposite and equal forces are applied between the relatively immovable cranium and/or neck and the tooth or teeth concerned, and difficulty has been experienced particularly with the use of unilateral or asymmetric headgear with which the clinician attempts to exert a greater distalization force upon the tooth or teeth on one side than the other.

The use of asymmetric headgear for differential distalization, in most cases, produces clinically undesirable side effects due primarily to the unwanted lateral forces that are applied to the molar as will hereinafter be described.

Attempts have been made in the past to overcome these disadvantages, one of which is the use of a combination inner arch and outer bow secured together with the outer bow being positioned asymmetrically to the side that requires excess distalization. However, analysis of the forces involved show that the undesirable lateral movement is still present.

SUMMARY OF THE INVENTION

The present invention overcomes these disadvantages by the use of a buttressed neck strap. It has been found that where cervically directed forces are required, the use of such a strap permits differential distalization without producing the undesired lateral force common to all conventional unilateral headgear solutions.

In accordance with the invention there is provided a neck band assembly for use in conjunction with an inner and outer bow appliance including strap anchoring or attachment means on the outer ends of the outer or facial bow; said neck band assembly comprising in combination a buttress component offset to one side of the appliance and a neck strap operatively secured thereto and extending upon either side thereof, said neck strap including a resilient portion and means on the outer ends of said neck strap for connecting same to the outer ends of the associated outer bow of the appliance, whereby differential forces are applied to the associated appliance with the greater force being applied to the side of the appliance upon which the buttress component is offset.

In accordance with another aspect of the invention, there is provided an orthodontic appliance for the generation of differential distal movement of teeth comprising in combination an inner and outer bow appliance, strap anchoring means formed on the outer ends of said outer bow, a buttress component offset to one side of the appliance and a neck strap operatively secured thereto and extending upon either side thereof, said neck strap including a resilient portion and means on the outer ends of said neck strap for connecting same to the outer ends of the associated outer bow of the appliance, whereby differential forces are applied to the associated appliance with the greater force being applied to the side of the appliance upon which the buttress component is offset.

In accordance with a still further aspect of the invention, there is provided a method of generating differential distal movement of teeth by means of apparatus which includes an inner and outer bow appliance and a resilient neck strap operatively secured thereto, said method including the application of a force upon one side of the appliance greater than the force being applied to the other side and offset to the tangential relationship of the neck strap with the neck of the patient.

Another advantage of the invention is that the adjustment of the buttressed neck strap is readily accomplished particularly on initial fitting merely by reducing the length and hence the thickness of the wide end of the buttress component.

Yet another advantage of the invention is to provide a device and method of the character herewithin described which is simple in construction, economical in manufacture and otherwise well suited to the purpose for which it is designed.

With the foregoing in view, and other advantages as will become apparent to those skilled in the art to which this invention relates as this specification proceeds, the invention is herein described by reference to the accompanying drawings forming a part hereof, which includes a description of the best mode known to the applicants and of the preferred typical embodiment of the principles of the present invention in which:

DESCRIPTION OF THE DRAWINGS

FIG. 1 is a schematic plan view of the system showing the lines of force generated and the like.

FIG. 3 is a rear elevation of the buttressed neck strap assembly.

FIG. 4 is a top plan view of FIG. 3.

FIG. 5 is a top plan view of the insert per se.

In the drawings like characters of reference indicate corresponding parts in the different figures.

DETAILED DESCRIPTION

The distal movement of teeth usually, but not always, requires that the teeth on one side have to be moved to a greater degree than those on the other and an asymmetrical outer bow is normally used in an attempt to apply a differential force depending upon the desired results so that for example, the ratio of the force is 75/25 although it will be appreciated that any desired relationship may be required.

With the use of a conventional neck band and an asymmetric facial bow, it has been found that the side or lateral thrust applied to the teeth being corrected was approximately in the same relationship thus giving undesirable results which may well be deleterious to the treatment being provided.

Figure 1:
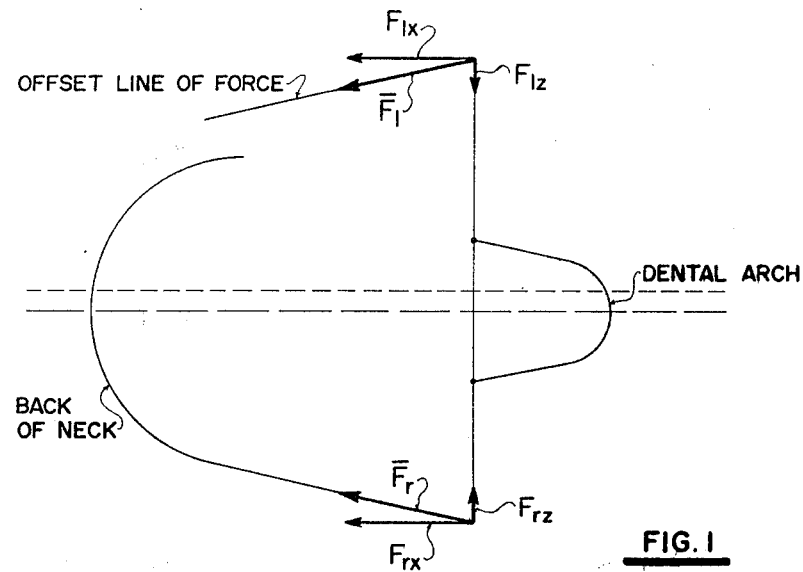
Figure 2:
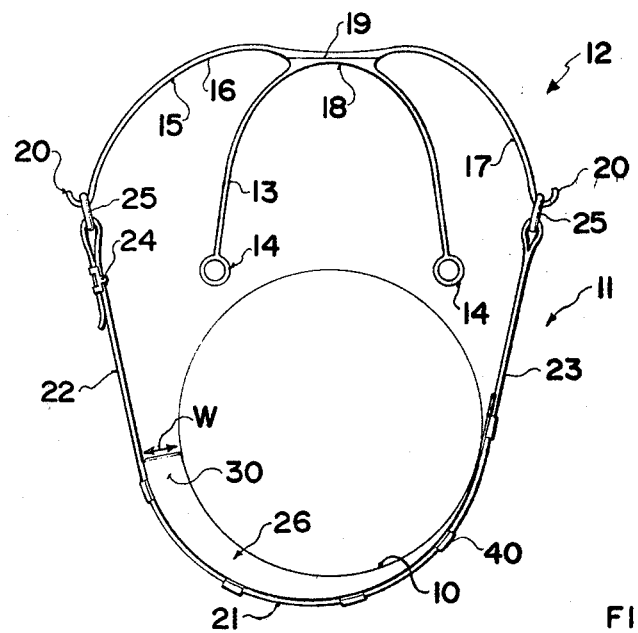
FIG. 2 is a schematic plan view of the appliance in position.

The present device overcomes these disadvantages and proceeding therefore to describe the invention in detail, reference should first be made to FIG. 1 which shows the forces encountered. In FIG. 2, reference character 10 represents the back of the neck around which the head band collectively designated 11 engages, when connected to a bow-type appliance collectively designated 12, which may be symmetrical or asymmetrical, depending upon design parameters.

Dealing first with the right-hand side, the vector $\bar{F}_r$ represents the force applied tangential to the neck curve. In accordance with mechanics, this vector $\bar{F}_r$ consists of the fore and aft component $F_{rx}$ and the lateral component $F_{rz}$ thus producing a moment about the vertical axis generated by $\bar{F}_r$ acting at a distance along the z axis from the centre of resistance.

In order to overcome this, the left-hand side should be noted. In the left-hand side, this moment is cancelled by making the left attachment point of the neck strap appropriately further from the centre of resistance than the right attachment point. This dictates that the line of action of the $\bar{F}_1$ must not be tangential to the outline of the neck but is offset by an amount decided upon by the clinician and depending upon the circumstances.

Reference to FIG. 2 will show the appliance which includes the inner bow 13 having tooth attachment pins 14 secured to the inner ends thereof or other equivalent tooth attachment means.

The outer or facial bow 15 includes the left segment 16 and the right segment 17 soldered to the approximate centre 18 of the inner or dental bow 13 as indicated by reference character 19. In FIG. 2, this outer bow is asymmetrical with the left portion extending outwardly and being slightly longer than the right portion 17. However, it will be appreciated that a symmetrical bow formation can be provided and that the left portion 16 can be shortened as necessary, depending upon the individual circumstances.

The outer ends of the portions 16 and 17 are provided with neck strap attaching means in the form of hooks 20, although other neck strap attaching means may be provided.

The neck strap 11 consists of an elongated strap preferably having a fabric or other material centre portion 21 with elasticized end portions 22 and 23 extending upon each side of the central portion. However, other constructions may of course be utilized.

A sliding adjustment clasp 24 of conventional construction is provided on one of the portions 22 or 23 and the outer ends of the portions 22 or 23 are provided with closed loops 25 which engage over the hooks 20 of the outer bow 15 when installed so that the adjustment clasp may be used to vary the tension applied to the appliance 12.

It will be appreciated that other appliance connecting means may be provided at the outer ends of the neck strap 12.

The buttress component collectively designated 26 is in the form of a wedge engaged between the strap and the neck 10 and on one side thereof as, for example, illustrated in FIG. 2 thus displacing the vector $\bar{F}_1$ a predetermined amount depending upon the requirements and being variable within limits, as will be described.

The component 26 preferably takes the form of a wedge-shaped fabric pocket 27 including a rear wall 28, a front wall 29 and opposed spaced and parallel side panels 30 increasing from an extremely narrow end 31 to the wide end 32 which is provided with a flexible closure cap or panel 33 secured by one end thereof to adjacent one end of the rear panel 28. This closure panel 33 may be in the open position shown in solid line in FIG. 4 or, alternatively, may be folded over the open end 32 and tucked in as indicated in phantom in FIG. 4.

A resilient insert 34 is provided for the pocket 27 and is preferably made from resilient foam either natural such as foam rubber or synthetic such as synthetic foam. It is cut in a wedge-shaped configuration and is provided with an extremely narrow end 35, a wide end 36, a rear wall 37, a front wall 38 and a pair of side walls 39 and is adapted to fit within the pocket 27 and be detachably maintained therein by the closure panel 33.

The walls 37 and 38 may be slightly curved to follow approximately the curvature of the neck or may be straight, relying upon the resiliency of the foam insert to mould to the neck contour.

Means are provided to detachably retain the buttress component 26 upon the neck strap 11 and to adjust same relative thereto. This takes the form of a plurality of vertically situated loops 40 secured in spaced and parallel relationship substantially along the longitudinal axis of the rear panel 28 of the pocket with the fabric portion 21 of the neck strap engaging through these loops and the resilient portions 22 and 23 extending at least through the outermost loops so that, when in place, and under tension due to the resilient portions 22 and 23, the buttress component remains substantially in the desired position with the wide end 30 facing towards the portion 16 of the outer bow as clearly shown in FIG. 2.

It will be observed that the width of the insert will control the amount of offset of the vector $F_1$ together with the length of the outer bow portion 16.

This positioning of the vector is readily adjusted by cutting off segments 34A, 34B, etc. of the wide end of the insert as indicated in phantom in FIG. 5 thus shifting the position of the vector $\bar{F}_1$ as necessary, depending upon the clinical requirements.

The length of the portion 16 together with the width of the wide part of the insert 34 also controls the relationship between vector $\bar{F}_1$ and $\bar{F}_r$ which may vary from equality on either side to any desired relationship.

It should of course be understood that the patient can rotate the head without disturbing the vector force relationships provided by the buttressed neck strap assembly.

Although the pocket 28 is preferably made of fabric, it may be made of elasticized fabric so that it will contract to the size and shape of the insert 34 thus preventing any wrinkling of the fabric to occur which might irritate the skin of the neck of the patient.

Since various modifications can be made in our invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

We claim:

1. A neck band assembly for use in conjunction with an inner and outer bow appliance including strap anchoring or attachment means on the distal ends of the outer or facial bow; said neck band assembly comprising in combination
    (a) a buttress component offset to one side of the appliance and;
    (b) a neck strap operatively secured thereto and extending upon either side thereof, said neck strap including a resilient portion and means on the outer ends of said neck strap for connecting same to the outer ends of the associated outer bow of the appliance, whereby differential forces are applied to the associated appliance with the greater force being applied to the side of the appliance upon which the buttress component is offset.

2. The assembly according to claim 1 in which said buttress component is wedge-shaped with the wide portion of the component being towards the said one end of the associated appliance.

3. The assembly according to claim 1 in which said neck strap is slidable relative to the buttress component.

4. The assembly according to claim 2 in which said neck strap is slidable relative to the buttress component.

5. The assembly according to claim 1 in which said neck strap is adjustable in length and hence is adjustable relative to the force exerted thereby upon said appliance.

6. The assembly according to claim 2 in which said neck strap is adjustable in length and hence is adjustable relative to the force exerted thereby upon said appliance.

7. The assembly according to claim 3 in which said neck strap is adjustable in length and hence is adjustable relative to the force exerted thereby upon said appliance.

8. The assembly according to claim 4 in which said neck strap is adjustable in length and hence is adjustable relative to the force exerted thereby upon said appliance.

9. The assembly according to claim 1 in which said buttress component includes a wedge-shaped fabric pocket and a resilient wedge-shaped insert detachably securable within said pocket and means to mount said neck strap on the outer side of said pocket.

10. The assembly according to claim 2 in which said buttress component includes a wedge-shaped fabric pocket and a resilient wedge-shaped insert detachably securable within said pocket and means to mount said neck strap on the outer side of said pocket.

11. The assembly according to claim 3 in which said buttress component includes a wedge-shaped fabric pocket and a resilient wedge-shaped insert detachably securable within said pocket and means to mount said neck strap on the outer side of said pocket, said means to mount said neck strap on the outer side of said pocket including a plurality of strap loops secured to said pocket, said neck strap sliding through said loops.

12. The assembly according to claim 4 in which said buttress component includes a wedge-shaped fabric pocket and a resilient wedge-shaped insert detachably securable within said pocket and means to mount said neck strap on the outer side of said pocket, said means to mount said neck strap on the outer side of said pocket including a plurality of strap loops secured to said pocket, said neck strap sliding through said loops.

13. The assembly according to claim 5 in which said buttress component includes a wedge-shaped fabric pocket and a resilient wedge-shaped insert detachably securable within said pocket and means to mount said neck strap on the outer side of said pocket.

14. The assembly according to claim 6 in which said buttress component includes a wedge-shaped fabric pocket and a resilient wedge-shaped insert detachably securable within said pocket and means to mount said neck strap on the outer side of said pocket.

15. The assembly according to claim 7 in which said buttress component includes a wedge-shaped fabric pocket and a resilient wedge-shaped insert detachably securable within said pocket and means to mount said neck strap on the outer side of said pocket, said means to mount said neck strap on the outside of said pocket including a plurality of strap loops secured to said pocket, said neck strap sliding through said loops.

16. The assembly according to claim 8 in which said buttress component includes a wedge-shaped fabric pocket and a resilient wedge-shaped insert detachably securable within said pocket and means to mount said neck strap on the outer side of said pocket, said means to mount said neck strap on the outerside of said pocket including a plurality of strap loops secured to said pocket, said neck strap sliding through said loops.

17. An orthodontic appliance for the generation of differential distal movement of teeth comprising in combination
 (a) an inner and outer bow appliance;
 (b) strap anchoring means formed on the outer ends of said outer bow;
 (c) a buttress component offset to one side of the appliance and;
 (d) a neck strap operatively secured thereto and extending upon either side thereof, said neck strap including a resilient portion and means on the outer ends of said neck strap for connecting same to the outer ends of the associated outer bow of the appliance, whereby differential forces are applied to the associated appliance with the greater force being applied to the side of the appliance upon which the buttress component is offset.

18. The assembly according to claim 17 in which said buttress component is wedge-shaped with the wide portion of the component being towards the said one end of the associated appliance.

19. The assembly according to claim 17 in which said neck strap is slidable relative to the buttress component.

20. The assembly according to claim 18 in which said neck strap is slidable relative to the buttress component.

21. The assembly according to claim 17 in which said neck strap is adjustable in length and hence is adjustable relative to the force exerted thereby upon said appliance.

22. The assembly according to claim 18 in which said neck strap is adjustable in length and hence is adjustable relative to the force exerted thereby upon said appliance.

23. The assembly according to claim 19 in which said neck strap is adjustable in length and hence is adjustable relative to the force exerted thereby upon said appliance.

24. The assembly according to claim 20 in which said neck strap is adjustable in length and hence is adjustable relative to the force exerted thereby upon said appliance.

25. The assembly according to claim 17 in which said buttress component includes a wedge-shaped fabric pocket and a resilient wedge-shaped insert detachably securable within said pocket and means to mount said neck strap on the outer side of said pocket.

26. The assembly according to claim 18 in which said buttress component includes a wedge-shaped fabric pocket and a resilient wedge-shaped insert detachably securable within said pocket and means to mount said neck strap on the outer side of said pocket.

27. The assembly according to claim 19 in which said buttress component includes a wedge-shaped fabric pocket and a resilient wedge-shaped insert detachably securable within said pocket and means to mount said neck strap on the outer side of said pocket, said means to mount said neck strap on the outer side of said pocket including a plurality of strap loops secured to said pocket, said neck strap sliding through said loops.

28. The assembly according to claim 20 in which said buttress component includes a wedge-shaped fabric pocket and a resilient wedge-shaped insert detachably securable within said pocket and means to mount said neck strap on the outer side of said pocket, said means to mount said neck strap on the outer side of said pocket including a plurality of strap loops secured to said pocket, said neck strap sliding through said loops.

29. The assembly according to claim 21 in which said buttress component includes a wedge-shaped fabric pocket and a resilient wedge-shaped insert detachably securable within said pocket and means to mount said neck strap on the outer side of said pocket.

30. The assembly according to claim 22 in which said buttress component includes a wedge-shaped fabric pocket and a resilient wedge-shaped insert detachably securable within said pocket and means to mount said neck strap on the outer side of said pocket.

31. The assembly according to claim 23 in which said buttress component includes a wedge-shaped fabric pocket and a resilient wedge-shaped insert detachably securable within the pocket and means to mount said neck strap on the outer side of said pocket, said means to mount said neck strap on the outerside of said pocket including a plurality of strap loops secured to said pocket, said neck strap sliding through said loops.

32. The assembly according to claim 24 in which said buttress component includes a wedge-shaped fabric pocket and a resilient wedge-shaped insert detachably securable within said pocket and means to mount said neck strap on the outer side of said pocket, said means to mount said neck strap on the outerside of said pocket including a plurality of strap loops secured to said pocket, said neck strap sliding through said loops.

33. The appliance according to claims 17, 18 or 19 in which said outer bow is asymmetrically secured to said inner bow with the longer side being upon the same side as said buttress component.

34. The appliance according to claims 20, 21 22 in which said outer bow is asymmetrically secured to said inner bow with the longer side being upon the same side as said buttress component.

35. The appliance according to claims 23, 24 or 25 in which said outer bow is asymmetrically secured to said inner bow with the longer side being upon the same side as said buttress component.

36. The appliance according to claims 26, 27 or 28 in which said outer bow is asymmetrically secured to said inner bow with the longer side being upon the same side as said buttress component.

37. The appliance according to claims 29, 30 or 31 in which said outer bow is asymmetrically secured to said inner bow with the longer side being upon the same side as said buttress component.

38. The appliance according to claim 32 in which said outer bow is asymmetrically secured to said inner bow with the longer side being upon the same side as said buttress component.

39. A method of generating differential distal movement of teeth by means of apparatus which includes an inner and outer bow appliance and a resilient neck strap operatively secured thereto, said method including the application of a force upon one side of the appliance greater than the force being applied to the other side and offset to the tangential relationship of the neck strap with the neck of the patient.

40. The method according to claim 39 in which the forces are adjustable.

* * * * *